(12) United States Patent
Habuchi et al.

(10) Patent No.: US 8,288,139 B2
(45) Date of Patent: Oct. 16, 2012

(54) SULFOTRANSFERASE INHIBITORS

(75) Inventors: Osami Habuchi, Nagoya (JP); Hirofumi Nakano, Kariya (JP); Toshihiko Sawada, Kitashitara-gun (JP); Sonoko Fujii, Marugame (JP); Shiori Ohtake, Tohashi (JP)

(73) Assignee: Seikagaku Corporation, Tokyo (JP)

( * ) Notice: Subject to any disclaimer, the term of this patent is extended or adjusted under 35 U.S.C. 154(b) by 150 days.

(21) Appl. No.: 12/194,353

(22) Filed: Aug. 19, 2008

(65) Prior Publication Data

US 2008/0318293 A1 Dec. 25, 2008

Related U.S. Application Data

(62) Division of application No. 10/520,659, filed as application No. PCT/JP03/08785 on Jul. 10, 2003, now abandoned.

(30) Foreign Application Priority Data

Jul. 10, 2002 (JP) .................................. 2002-201843
Dec. 27, 2002 (JP) .................................. 2002-382122

(51) Int. Cl.
*C12N 9/99* (2006.01)
*C07H 17/02* (2006.01)
(52) U.S. Cl. ...................................... 435/184; 536/17.5
(58) Field of Classification Search ........................ None
See application file for complete search history.

(56) References Cited

U.S. PATENT DOCUMENTS

| 4,404,365 | A | 9/1983 | Miner |
| 6,265,192 | B1 | 7/2001 | Bistrup et al. |
| 6,365,365 | B1 | 4/2002 | Bistrup et al. |
| 2005/0004069 | A1 | 1/2005 | Uzawa et al. |

FOREIGN PATENT DOCUMENTS

| WO | 97/00879 A1 | 1/1997 |
| WO | 00/11208 A1 | 3/2000 |
| WO | 02/103025 A | 12/2002 |

OTHER PUBLICATIONS

Sawada et al. Carbohydrate Research 340 (2005) 1983.*
Nozaki et al. Glycoconj J (2010) 27:237-248.*
Rath et al. DDT vol. 9, No. 23, Dec. 2004.*
Skelton et al. The Journal of Biological Chemistry, vol. 266, No. 26, Sep. 15, pp. 17142-17150, 1991.*
Pocklington et al. Biochem. J. (1969) 112, 331.*
Clinch K et al.: "Synthesis and utility of sulfated chromogenic carbohydrate model substrates for measuring activities of mucin-desulfating enzymes" Carbohydrate Research, Pergamon, GB LINKD—DOI:10.1016/S0008-6215(02)00104-0, vol. 337, No. 12, Jun. 12, 2002, pp. 1095-1111, P004370565, ISSN: 0008-6215.
H. Uzawa et al.: "synthetic potential of molluscan sulfatases for the library synthesis of regioselectively o-sulfonated d-galacto-sugars" ChemBioChem, vol. 4, No. 7, Apr. 2003 , pp. 640-647, XP002576797 einheim.

Supplementary European Search Report dated Apr. 16, 2010, issued in counterpart European Application No. 03764162.8-1211.
European Patent Office, Communication from the European Patent Office dated Apr. 20, 2011, in counterpart Application No. 03764162.8.
Osami Habuchi et al., Sulfation of *p*-Nitrophenyl-*N*-acetyl-β-D-galactosaminide with a Microsomal Fraction from Cultured Chondrocytes, The Journal of Biological Chemistry, 1985, 260(24): 13102-13108.
Paul E. Fraser et al., "Amyloid-β Interactions with Chondroitin Sulfate-derived Monosaccharides and Disaccharides", The Journal of Biological Chemistry, 2001, 276(9): 6412-6419.
Kiyoshi Ikeda et al., Synthesis of *N*-Acetylglucosaminyl- and *N*-Acetylgalactosaminylceramides as Cerebroside Analogs and Their Anti-human Immunodeficiency Virus Type 1 Activities, Chem. Pharm. Bull., 1997, 45(2): 402-405.
Barbara Faroux-Corlay et al., "Synthesis of single- and double-chain fluorocarbon and hydrocarbon galactosyl amphiphiles and their anti-HIV-1 activity", Carbohydrate Research, 2000, 327: 223-260.
Tina Horrobin et al., Esterase-catalysed segioselective 6-deacylation of hexopyranose per-acetates, acid-catalysed rearrangement to the 4-deprotected products and conversions of these into hexose 4- and 6-sulfates, J. Chem. Soc., Perkin Trans.1, 1998, 1069-1080.
Kazuyuki Sugahara et al., "Regulation of Serum Glycosaminoglycan Sulfotransferase Activities: Inhibition by Sulfated Glycosaminoglycans and Activation by Polyamines and Basic Peptides Including a Polylysine-Containing Segment of the c-Ki-*ras* 2 Protein", J. Biochem., 1989, 106: 910-919.
International Search Report Issued in PCT/JP2003/08785, dated Oct. 28, 2003.
Shiori Ohtake et al., "Human *N*-Acetylgalactosamine 4-Sulfate 6-*O*-Sulfotransferase cDNA is Related to Human B Cell Recombination Activating Gene-associated Gene", The Journal of Biological Chemistry, 2001, 276(47): 43894-43900.
Lars Uhlin-Hansen et al., "Modulation of the Expression of Chondroitin Sulfate Proteoglycan in Stimulated Human Monocytes", The Journal of Biological Chemistry, 1989, 264(25):14916-14922.

(Continued)

*Primary Examiner* — Layla Bland
(74) *Attorney, Agent, or Firm* — Sughrue Mion, PLLC (57) ABSTRACT

A galactosamine derivative represented by the following formula (1):

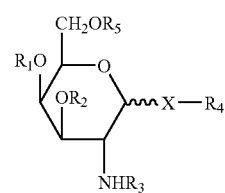

wherein $R_1$, $R_2$ and $R_5$ each independently represents $SO_3^-$ or H, and at least one of them represents $SO_3^-$; $R_3$ represents H, acetyl or $SO_3^-$; $R_4$ represents H, a substituted or unsubstituted alkyl group, a substituted or unsubstituted alkenyl group, a substituted or unsubstituted alkynyl group, a substituted or unsubstituted acyl group, a substituted or unsubstituted aryl group, or a substituted or unsubstituted aralkyl group; X represents O, S, NH or $CH_2$; and ⁓ represents an α bond or a β bond, and a sulfotransferase inhibitor comprising the derivative.

10 Claims, 3 Drawing Sheets

OTHER PUBLICATIONS

Glen L. Hortin et al., "Inhibitors of the Sulfation of Proteins, Glycoproteins, and Proteoglycans", Biochemical and Biophysical Research Communications, 1988, 150(1):342-348.

Geetha Sugumaran et al., "Effects of Brefeldin A on the Localization of Chondroitin Sulfate-synthesizing Enzymes", The Journal of Biological Chemistry, 1992, 267(13):8802-8806.

Theodora W. Greene et al., "Protective Groups in Organic Synthesis", Third Edition, John Wily & Sons, Inc., 1999, pp. 99-100.

Florencio Zaragoza Dorwald, "Side Reactions in Organic Synthesis", Wiley: VCH, Weinheim, 2005, pp. IX of Preface.

Boris Vauzeilles et al., "A one-step-selective glycosylation of N-acetyl glucosamine and recombinant chitooligosaccharides", Tetrahedron Letters, 2001, 42: 7567-7570.

* cited by examiner

SULFOTRANSFERASE INHIBITORS

CROSS-REFERENCE TO RELATED APPLICATIONS

This is a divisional of application Ser. No. 10/520,659 filed Jan. 10, 2006, which is a 371 National Stage Entry of PCT/JP2003/08785 filed Jul. 10, 2003. The entire disclosures of the prior applications, application Ser. Nos. 10/520,659 and PCT/JP2003/08785 are considered part of the disclosure of the accompanying divisional application and are hereby incorporated by reference.

TECHNICAL FIELD

The present invention relates to a sulfotransferase inhibitor, more particularly to an inhibitor which inhibits activity of a sulfotransferase (hereinafter sometimes referred to as "GalNAc4S6ST") having activity of activating sulfation of a hydroxyl group bound to the 6-position of the 4-sulfated galactosamine residue contained in the basic backbone of chondroitin sulfate as a kind of glycosaminoglycans.

BACKGROUND OF THE INVENTION

Chondroitin sulfate is a kind of glycosaminoglycans, which is a polysaccharide having a backbone in which a disaccharide resulting from the bonding of glucuronic acid and N-acetylgalactosamine via 1-3 glycosidic linkage is connected in a row via 1-4 glycosidic linkage (hereinafter also referred to as "basic backbone") and having sulfate groups.

In addition to the glycosaminoglycans such as chondroitin sulfate, in many cases, proteoglycans, glycoproteins and glycolipids have sulfate groups, and many types of sulfotransferases relate to their biosyntheses. Particularly, it has been suggested that the enzyme described in *J. Biol. Chem.*, 276, 43894-43900 (2001), chondroitin sulfate formed thereby (*J. Biol. Chem.*, 264, 14916-14922 (1989)) and the like deeply relate to the immune system, nervous system or inflammatory reactions, and inhibitors of the enzymes have a high possibility of being able to apply to an immunosuppressive agent (e.g., therapeutic agent for atopic dermatitis, asthma and Crohn disease, etc.) and a nerve controlling agent and a disease treating agent (e.g., therapeutic agent, nerve repair controlling agent, anti-inflammatory agent, etc. for neurosis, Alzheimer disease, maniac-depressive psychosis, psychosis, autonomic imbalance, nervous enteritis, etc.) (U.S. Pat. Nos. 6,265,192, 6,365,365, etc.).

As such sulfotransferase inhibitors, for example, the chlorate described in *Biochem. Biophys. Res. Commun.*, 150, 342-348 (1988), the brefeldin A described in *J. Biol. Chem.*, 267, 8802-8806 (1992) and the like are present. However, since the former shows nonspecific antagonism upon the sulfate group transfer by a sulfotransferase, and the latter destroys the Golgi body which is the field of sugar chain synthesis, they have activity of strongly inhibiting biosynthesis of not only chondroitin sulfate but also other glycosaminoglycans and glycoproteins, so that their possibility to be used as therapeutic agents was extremely low.

Accordingly, concern has been directed toward a novel compound having highly specific inhibitory activity for a specified sulfotransferase, and a novel sulfotransferase inhibitor which uses the same.

DISCLOSURE OF THE INVENTION

The present invention relates to the following (1) to (11).
(1) A galactosamine derivative represented by the following formula (1):

wherein $R_1$, $R_2$ and $R_5$ each independently represents $SO_3^-$ or H, and at least one of them represents $SO_3^-$;
$R_3$ represents H, acetyl or $SO_3^-$;
$R_4$ represents H, a substituted or unsubstituted alkyl group, a substituted or unsubstituted alkenyl group, a substituted or unsubstituted alkynyl group, a substituted or unsubstituted acyl group, a substituted or unsubstituted aryl group, or a substituted or unsubstituted aralkyl group;
X represents O, S, NH or $CH_2$; and
∼∼ represents an α bond or a β bond.
(2) The galactosamine derivative according to the above (1), wherein $R_1$ and $R_2$ each is H; $R_3$ is an acetyl group; $R_4$ is a substituted or unsubstituted aryl group; and $R_5$ is $SO_3^-$.
(3) The galactosamine derivative according to the above (1), wherein $R_1$ is $SO_3^-$; $R_2$ and $R_5$ each is H; $R_3$ is an acetyl group; and $R_4$ is a substituted or unsubstituted aryl group.
(4) The galactosamine derivative according to the above (1), wherein $R_1$ and $R_5$ each is H; $R_2$ is $SO_3^-$; $R_3$ is an acetyl group; and $R_4$ is a substituted or unsubstituted aryl group.
(5) A sulfotransferase inhibitor which comprises the galactosamine derivative according to any one of the above (1) to (4).
(6) The sulfotransferase inhibitor according to the above (5), which inhibits activity of a sulfotransferase having activity of transferring a sulfate group to a hydroxyl group bound to the 6-position carbon atom on the 4-sulfated galactosamine residue in the basic backbone of chondroitin sulfate.
(7) A method for inhibiting activity of a sulfotransferase, which comprises allowing the galactosamine derivative according to any one of the above (1) to (4) to be present in an enzyme reaction system of the sulfotransferase.
(8) Use of the galactosamine derivative according to any one of the above (1) to (4) as a sulfotransferase inhibitor.
(9) Use of the galactosamine derivative according to any one of the above (1) to (4) for producing a sulfotransferase inhibitor.
(10) A medicament based on inhibition of sulfotransferase activity, which comprises the galactosamine derivative according to any one of the above (1) to (4) as an active ingredient.
(11) A medicament for treating or preventing diseases caused by acceleration of sulfotransferase activity, which comprises the galactosamine derivative according to any one of (1) to (4) as an active ingredient.

BEST MODE FOR CARRYING OUT THE INVENTION

In order to solve the above-described problems, the present inventors have conducted intensive studies and found as a result that a "galactosamine derivative" in which an aglycone molecule is bound to an anomeric carbon of "galactosamine wherein the 3-position, 4-position and/or 6-position carbon atom is sulfated" via a glycosidic linkage has excellent inhibitory activity upon a sulfotransferase, particularly GalNAc4S6ST, thus accomplishing the present invention.

The present invention is described below in detail based on the embodiments of the present invention.

(1) Substance of the Present Invention

The substance of the present invention is a galactosamine derivative which is represented by the following formula (1):

Sulfated galactosamine residue moiety

In the formula, $R_1$, $R_2$ and $R_5$ each independently represents $SO_3^-$ (sulfate group) or H (hydrogen atom), wherein at least one of them is $SO_3^-$; $R_3$ represents H, an acetyl group or $SO_3^-$; $R_4$ represents H, a substituted or unsubstituted alkyl group, a substituted or unsubstituted alkenyl group, a substituted or unsubstituted alkynyl group, a substituted or unsubstituted acyl group, a substituted or unsubstituted aryl group, or a substituted or unsubstituted aralkyl group; X represents O, S, NH or $CH_2$, and represents an α bond or a β bond.

In the sulfated galactosamine residue moiety (the part indicated as the "sulfated galactosamine residue moiety" in the above-described formula) constituting the sulfated galactosamine derivative represented by formula (1) which is the substance of the present invention, the 2-position amino group of the sulfated galactosamine residue may be acetylated or sulfated, and in particular, preferably acetylated. That is, $R_3$ is H, an acetyl group or $SO_3^-$, particularly preferably an acetyl group.

In addition, hydrogen atoms of the hydroxyl groups bound to the 3-position, 4-position and 6-position carbon atoms of the sulfated galactosamine residue may be each independently substituted with $SO_3^-$, and it is necessary that at least one of these carbon atoms is sulfated. That is, $R_1$, $R_2$ and $R_5$ in the above-described formula are each independently $SO_3^-$ or H, and it is necessary that at least one of them is $SO_3^-$. Most preferably, only one of $R_1$, $R_2$ and $R_5$ is $SO_3^-$ and each of the others is H.

The moiety of $R_4$ represented by the formula (1) is a hydrogen atom (H) or an aglycone molecule generally used in the modification or protection of saccharides, and an aglycone molecule is more preferable than a hydrogen atom. Examples of the aglycone molecule include a substituted or unsubstituted alkyl group, a substituted or unsubstituted alkenyl group, a substituted or unsubstituted alkynyl group, a substituted or unsubstituted acyl group, a substituted or unsubstituted aryl group, and a substituted or unsubstituted aralkyl group A substituted or unsubstituted aryl group and a substituted or unsubstituted aralkyl group are preferred, and a substituted or unsubstituted aryl group is particularly preferred.

Examples of the above-described alkyl group include a liner or branched-chain alkyl group having from 1 to 23, preferably from 2 to 20, carbon atoms, and the preferred alkyl group includes a linear alkyl group having from 2 to 18 carbon atoms. In addition, the alkyl group may be an alkoxyalkyl group having an alkylglycerol-derived backbone or an acyloxyalkyl group having an acylglycerol-derived backbone as shown in the following formula (2) (in the following structural formula, l and m each independently represents an integer of from 0 to 18; and Z's each independently represents a methylene group or a carbonyl group).

The above-described alkenyl group and alkynyl group preferably have from 1 to 23, preferably from 2 to 20, carbon atoms, and they may have two or more carbon-carbon double bonds and triple bonds.

The above-described acyl group may be any group which is generally represented by —CO—R, but the moiety represented by R has from 1 to 23, preferably from 2 to 20, carbon atoms. Also, R in the above-described formula is a group selected from an alkyl group, an alkenyl group and an alkynyl group described above, and an aryl group and an aralkyl group described below.

The alkyl group, the alkenyl group, the alkynyl group and the acyl group may be further substituted with a hydroxyl group (OH), an oxo group, a halogen atom, a substituted or unsubstituted aryl group, a substituted or unsubstituted heterocyclic group, a nitro group, a substituted or unsubstituted amino group, a trifluoromethyl group, a substituted or unsubstituted alkylthio group, a substituted or unsubstituted aryloxy group, a substituted or unsubstituted carbamoyl group, a mercapto group, or a cyano group. Also, examples of the substituent of the substituted heterocyclic group, the substituted amino group, the substituted alkylthio group, the substituted aryloxy group and the substituted carbamoyl group include a hydroxyl group (OH), an oxo group, and a halogen atom. Also, examples of the heterocyclic group include a 3- to 8-membered heterocyclic group containing at least one atom selected from a nitrogen atom, an oxygen atom and a sulfur atom.

Examples of the above-described aryl group include an aromatic hydrocarbon residue such as a phenyl group and a naphthyl group, and an aromatic residue in which a hydrogen atom on the aromatic ring in the above-described aromatic hydrocarbon residue is substituted with a substituent such as an alkyl group, an acyl group, a hydroxyl group (OH), a halogen atom (fluorine atom (F), chlorine atom (Cl), bromine atom (Br), iodine atom (I), etc.), a nitro group (NO$_2$), a sulfate group (SO$_3^-$) or an oxo group (e.g., alkoxyphenyl group, tolyl group, etc.), and among these, a phenyl group and a naphthyl group are preferred and a phenyl group is particularly preferred.

The above-described aralkyl group is a residue represented by a formula Ar—(CH$_2$)$_n$— in which an alkyl group is bound to the above-described substituted or unsubstituted aryl group (Ar), wherein n is preferably from 1 to 20, more preferably from 2 to 18. Examples of the aralkyl group include a benzyl group, a phenetyl group, an α-methylbenzyl group and the like.

Binding of the "sulfated galactosamine residue moiety" to R$_4$ in the above-described formula (1) is a glycosidic linkage via the 1-position carbon atom of a sulfated galactosamine derivative residue of the "sulfated galactosamine residue moiety", and this may be either an α-glycosidic linkage or a β-glycosidic linkage (the linkage shown by a wave line ∼∼∼ in formula (1)). In addition, the glycosidic linkage according to the present invention includes, for example, not only an O-glycosidic linkage in the basic backbone of general glycosaminoglycans but also an S-glycosidic linkage, an N-glycosidic linkage and a C-glycosidic linkage in which the O (an oxygen atom) moiety is respectively substituted with S (sulfur atom), NH (imino group) and CH$_2$ (methylene group). However, according to the present invention, an O-glycosidic linkage is particularly preferred. That is, X in the above-described formula includes O, S, NH and CH$_2$, and O is most preferable. Also, the 6-membered ring constituting the saccharide can exist in either a boat conformation or a chair conformation, but a chair conformation is preferred according to the substance of the present invention from the stability point of view. However, the conformation is not limited thereto.

Thus, examples of most preferable sulfated galactosamine glycoside derivatives include substances represented by the following formula (3), formula (4), formula (5), formula (6) and the like:

(3)

(4)

(5)

(6)

In these formulae, Ac represents an acetyl group. The wave line ∼∼∼ represents α and β as the mode of the glycosidic linkage to the sulfated galactosamine residue moiety. For the sake of convenience, the α-linked substance of the present invention represented by the above-described formula (3) is called "Substance 1 of the present invention", and the β-linked substance of the present invention represented by the above-described formula (3) is called "Substance 2 of the present invention". In the same manner, the α-linked substance of the present invention represented by the above-described formula (4) is called "Substance 3 of the present invention", and the β-linked substance of the present invention represented by the above-described formula (4) is called "Substance 4 of the present invention", the α-linked substance represented by the above-described formula (5) is called "Substance 5 of the present invention", and the β-linked substance represented by the above-described formula (5) is called "Substance 6 of the present invention".

Substances 1 and 2 of the present invention can be prepared by the following method.

That is, they can be synthesized by dissolving phenyl 2-acetamide-2-deoxy-D-galactopyranoside in dry pyridine, adding a sulfur trioxide-pyridine complex thereto to carry out the reaction, and then selectively sulfating the 6-position hydroxyl group. After the reaction, the resulting product is subjected to ion exchange and concentrated to obtain Substance 1 or 2 of the present invention. After the above-described reaction, if necessary, it is possible to carry out purification by using a methods which separate compounds based on their molecular weight such as chromatography using an ion exchange resin or gel filtration.

Also, Substances 3 and 4 of the present invention can be prepared by the following method. That is, 2-acetamide 4,6-O-benzylidene-2-deoxy-D-galactopyranoside is dissolved in dry pyridine, a sulfur trioxide-pyridine complex is added thereto, followed by stirring by heating at, for example, 50° C. for 4 hours or more to thereby sulfate the 3-position hydroxyl group. Next, methanol is added thereto, followed by concentration, to thereby obtain a reaction product, and the reaction product is dissolved in an aqueous ethanol solution. A palladium catalyst is added to the solution and the reaction is carried out in hydrogen gas atmosphere to remove a benzylidene group, followed by filtering through celite or the like, and then purification is carried out according to a usual method to prepare Substance 3 or 4 of the present invention.

In addition, Substances 5 and 6 of the present invention can be synthesized by dissolving phenyl 2-acetamide-2-deoxy-4-O-sulfonyl-6-O-benzyl-D-galactopyranoside in an aqueous ethanol solution or the like, and adding a palladium catalyst thereto to carry out the reaction in hydrogen gas atmosphere to thereby remove the 6-position benzyl group. Next, the reaction mixture is filtered through celite or the like and purified according to a usual method to obtain Substances 5 and 6 of the present invention.

The function of the substances of the present invention obtained in this manner as the following inhibitor of the present invention can be confirmed by allowing a sulfotransferase (particularly the sulfotransferase described in *J. Biol. Chem.*, 276, 43894-43900 (2001)) and the substrates of the enzyme (sulfate group donor and sulfate group acceptor) to coexist and measuring the enzyme activity of the sulfotransferase.

(2) Inhibitor of the Present Invention

The inhibitor of the present invention comprises the substance of the present invention and has function of inhibiting the activity of a sulfotransferase.

The sulfotransferase whose activity is inhibited by the inhibitor of the present invention is an enzyme having activity of transferring a sulfate group from a sulfate group donor to a sulfate group acceptor, and is preferably an enzyme having activity of sulfating a hydroxyl group bound to the 4-position carbon atom of the galactosamine in the basic backbone of chondroitin or an enzyme which transfers a sulfate group to the 6-position hydroxyl group of a hexosamine residue in the basic backbone of glycosaminoglycan, and particularly, the latter enzyme is preferred. Examples of the enzyme include enzymes described in JP-A-10-33168, JP-A-2001-57882, *J. Biol. Chem.*, 276, 43894-43900 (2001), JP-A-2000-60566, WO02/00889, JP-A-2001-61481 and JP-A-8-33483, and among these, the chondroitin 6-sulfotransferase which is an enzyme capable of transferring a sulfate group to the galactosamine residue in chondroitin sulfate (JP-A-10-33168, JP-A-2001-57882, *J. Biol. Chem.*, 276, 43894-43900 (2001)) is particularly preferred, and the enzyme described in *J. Biol. Chem.*, 276, 43894-43900 (2001) (an enzyme having activity of transferring a sulfate group to the 6-position hydroxyl group of the 4-sulfated galactosamine residue in chondroitin sulfate: GalNAc4S6ST) is most preferred.

According to the inhibitor of the present invention, the "inhibitory activity of enzyme activity" means a case where, when the enzyme activity in a reaction system to which the inhibitor of the present invention is not added (control) is regarded as 100% and the enzyme activity to which the enzyme is not added (negative control) is regarded as 0%, the enzyme activity is reduced by a factor of 5% or more in comparison with the control. The inhibitor of the present invention shows 5% or more, preferably 10% or more, most preferably 15% or more, of the inhibitory activity at the time of the reaction with an inhibitor concentration of 2.5 mM, particularly when the inhibitory activity is measured according to the inhibitory activity measuring method described in the following Example 2.

It is possible to use the inhibitor of the present invention which is a preventive or therapeutic agent for diseases caused by acceleration of activity of an enzyme capable of transferring a sulfate group to the basic backbone of chondroitin, particularly of GalNAc4S6ST, or diseases in which delay of advance of symptoms and improvement or prevention of symptoms can be carried out by inhibiting the activity of GalNAc4S6ST. Specifically, it is possible to apply it to a preventive agent, a therapeutic agent or the like for allergy, inflammation, nervous ataxia, neurological disorder or the like. Accordingly, it is also possible to use the inhibitor of the present invention in combination with a conventionally known anti-allergic drug, anti-inflammatory drug, nervous ataxia treating agent, neurological disorder treating agent or the like.

In addition, it is possible to provide the inhibitor of the present invention as a pharmaceutical preparation which is produced according to any method well known in the technical field of manufacturing pharmacy, by mixing it with at least one pharmaceutically acceptable carrier. Examples of the carrier include components generally used in medicaments such as a stabilizing agent, an emulsifying agent, an osmotic pressure controlling agent, a buffering agent, a tonicity agent, a preservative, a soothing agent, a coloring agent, an excipient, a binder, a lubricant, a disintegrating agent, a surfactant and the like.

As an administration route, most effective one in treatment is used, and examples include oral administration and parenteral administration such as transnasal, transmucosal, tracheal, rectal, subcutaneous, intramuscular and intravenous administration.

The dose or administration frequency varies depending on the intended therapeutic effect, administration method, treating period, age, body weight and the like, but is generally from about 1 mg to about 1,000 mg per day per adult, once to several times a day.

Example 1

Preparation of the Substances of the Present Invention (1) Preparation of Substance 1 of the Present Invention Compound 1

Compound 2

In 1.5 cm³ of dry pyridine, 21.7 mg (0.073 mmol) of phenyl 2-acetamide-2-deoxy-α-D-galactopyranoside (Compound 1) was dissolved, and 20.1 mg (0.126 mmol) of sulfur trioxide-pyridine complex was added thereto, followed by stirring at room temperature for 6 hours. To the reaction mixture, 1.5 cm³ of methanol was added, and the mixture was passed through a column of Na⁺ type ion exchange resin (PARTISIL10SAX, manufactured by Whatman), and the eluate was concentrated under reduced pressure to obtain 34.4 mg of Compound 2 (Substance 1 of the present invention). Compound 2 was purified by high performance liquid chromatography (HPLC) using a column of ion exchange resin (PARTISIL10SAX, manufactured by Whatman) and by gel filtration (using a Superdex 30 column, manufactured by Pharmacia Biotech). Substance 1 of the present invention prepared in this manner was analyzed by ¹H-NMR. Also, the "Ph" in the above chemical formula indicates a phenyl group.

Compound 2:

¹H-NMR (400 MHz, D$_2$O) δ (ppm): 1.92 (s, 3H, NHCOCH$_3$), 3.97-4.10 (m, 4H), 4.23-4.27 (m, 2H), 5.44 (d, 1H, J=3.7 Hz, α-H-1), 7.00-7.04 (m, 3H), 7.24-7.28 (m, 2H)

(2) Preparation of Substance 2 of the Present Invention

Compound 3

Compound 4

In 2.0 cm³ of dry pyridine, 40.4 mg (0.1358 mmol) of phenyl 2-acetamide-2-deoxy-β-D-galactopyranoside (compound 3) was dissolved, and 44.5 mg (0.2781 mmol) of sulfur trioxide-pyridine complex was added thereto, followed by stirring at 24° C. for 6 hours. To the reaction mixture, 1.5 cm³ of methanol was added, and the mixture was passed through a column of Na⁺ type ion exchange resin (Dowex 50W, manufactured by Dow Chemical), and the eluate was centrifuged to remove unnecessary substances and then concentrated under reduced pressure to obtain 5.0 mg of Compound 4 (Substance 2 of the present invention). Compound 4 was purified by high performance liquid chromatography (HPLC) using a column of ion exchange resin (PARTISIL10SAX, manufactured by Whatman) and by gel filtration (using a Superdex 30 column, manufactured by Pharmacia Biotech). Substance 2 of the present invention prepared in this manner was analyzed by ¹H-NMR. Also, the "Ph" in the above chemical formula indicates a phenyl group.

Compound 4:

Yield: 9%

¹H-NMR (400 MHz, D$_2$O) δ (ppm): 1.88 (s, 3H, NHCOCH$_3$), 3.72 (d, 1H, J=11.5 Hz, H-3), 3.93 (s, 1H, H-4), 3.97-4.15 (m, 4H, H-6, H-5, H-2), 4.94 (d, 1H, J=8.3 Hz, β-H-1), 6.94-7.03 (m, 3H), 7.22-7.28 (m, 2H)

(3) Preparation of Substance 3 of the Present Invention

Compound 5

Compound 6

In 2.0 cm³ of dry pyridine, 30.4 mg (0.0788 mmol) of 2-acetamide 4,6-O-benzylidene-2-deoxy-α-D-galactopyranoside (Compound 5) was dissolved and 134.3 mg (0.3395 mmol) of sulfur trioxide-pyridine complex was added thereto. The mixture was stirred for 20 hours under heating at 50° C., and then 2.0 cm³ of methanol was added thereto. After the reaction was finished, the mixture was passed through a column of Na⁺ type ion exchange resin and concentrated. The residue was purified by silica gel column chromatography.

In 2.0 cm³ of an aqueous ethanol solution, 18.5 mg (0.0379 mmol) of this purified product was dissolved, and 21.2 mg of a palladium catalyst (palladium-carbon) was added to this solution, followed by stirring for 33 hours under heating at 40° C. in hydrogen gas atmosphere. After the reaction was finished, the mixture was filtered through celite and then purified by electrophoresis and gel filtration to obtain Compound 6 (Substance 3 of the present invention) (3.9 mg). Also, the "Ph" in the above chemical formula indicates a phenyl group.

Compound 6:

Yield: 26%

¹H-NMR (400 MHz, D$_2$O) δ (ppm): 1.91 (s, 3H, NHCOCH$_3$), 3.60 (d, 2H, J=6.1 Hz, H-6), 4.01 (t, 1H, J=6.1 Hz, H-5), 4.26 (d, 1H, J=3.2 Hz, H-4), 4.43 (dd, 1H, J=10.7 Hz, J=3.7 Hz, H-2), 4.62-4.69 (m, 1H, H-3), 5.55 (d, 1H, J=3.7 Hz, α-H-1), 6.99-7.06 (m, 3H), 7.24-7.26 (m, 2H)

¹³C-NMR (100.4 MHz, D$_2$O) δ (ppm): 24.82, 50.65, 63.75, 74.41, 78.50, 99.09, 120.03, 126.06, 132.72, 158.75, 177.61

(3) Preparation of Substance 6 of the Present Invention

Compound 7

Compound 8

In 2.0 cm³ of an aqueous ethanol solution, 16.2 mg (0.0279 mmol) of phenyl 2-acetamide-2-deoxy-4-O-sulfonyl-6-O-benzyl-β-D-galactopyranoside (Compound 7) was dissolved and 30.4 mg of palladium catalyst (palladium-carbon) was added thereto. The mixture was stirred for 21 hours under heating at 40° C. in hydrogen gas atmosphere. After filtering the mixture through celite, it was purified using a column of ion exchange resin and by gel filtration chromatography. The preparation was carried out in this manner to obtain 5.2 mg of Compound 8 (Substance 6 of the present invention). Also, the "Bn" in the above chemical formula indicates a benzyl group, and the "Ph" indicates a phenyl group.

Compound 8:

Yield: 47%

(4) Preparation of Other Substances of the Present Invention

Compound 9

Compound 10

After 103.2 mg (0.315 mmol) of Compound 9 (D-galactosamine derivative) was mixed with 1.55 cm³ of dry dichloromethane, and 1.05 cm³ of pyridine was added thereto. The mixture was cooled to 0° C., and 0.125 cm³ of pivaloyl chloride (d=0.979, 1.0149 mmol) was added thereto, followed by stirring at room temperature for 15.5 hours. To the reaction mixture, 0.10 cm³ of pivaloyl chloride (0.812 mmol) was further added, followed by stirring at room temperature for 7 hours, dissolved in 50 cm³ of chloroform and then washed with 15 cm³ of saturated aqueous sodium bicarbonate solution three times and with 15 cm³ of saturated brine three times. The organic layer was dried with anhydrous sodium sulfate and concentrated under reduced pressure. As the residual material was separated and purified by silica gel column chromatography (ethyl acetate-hexane), 102.6 mg (0.207 mmol) of Compound 10 was obtained as colorless oil.
Compound 10:
Yield: 66%
Rf=0.278 (50% ethyl acetate-hexane development once)
$^1$H NMR (400 MHz, CDCl$_3$) δ (ppm): 1.08 (s, 9H, C(C$\underline{H}_3$)$_3$), 1.21 (s, 9H, C(CH$_3$)$_3$), 1.93 (s, 3H, NHCOCH$_3$), 3.75 (s, 3H, OCH$_3$), 4.03 (m, 1H, H-4), 4.13-4.21 (m, 2H, H-5 and H-6a), 4.33 (dd, J$_{6a,6b}$=1.0 Hz, J$_{5,6b}$=3.9 Hz, H-6b), 4.83 (ddd, J$_{2,3}$=11.0 Hz, J$_{2,NH}$=10.2 Hz, J$_{1,2}$=3.6 Hz, H-2), 5.30 (dd, J$_{2,3}$=1.0 Hz, J$_{3,4}$=3.2 Hz, H-3), 5.43 (d, J$_{1,2}$=3.6 Hz, H-1), 5.76 (d, J$_{2,NH}$=10.2 Hz, NH), 6.78-6.82 (m, 2H, arom. H), 6.96-7.00 (m, 2H, arom. H)
$^{13}$C NMR (100.4 MHz, CDCl$_3$) δ (ppm): 23.26 (q, NHCOC$\underline{H}_3$), 27.03 (q, C(C$\underline{H}_3$)$_3$), 27.07 (q, C(C$\underline{H}_3$)$_3$), 38.65 (s, $\underline{C}$(CH$_3$)$_3$), 39.09 (s, $\underline{C}$(CH$_3$)$_3$), 47.42 (d, C-2), 55.68 (q, O$\underline{C}$H$_3$), 63.30 (t, C-6), 67.72 (d, C-4), 69.10 (d, C-5), 70.31 (d, C-3), 97.19 (d, C-1), 114.75 (d, arom. CH), 117.76 (d, arom. CH), 150.10 (s, arom. C), 155.35 (s, arom. C), 169.86 (s, NHCOCH$_3$), 178.32 (s, O=$\underline{C}$C(CH$_3$)$_3$), 178.56 (s, O=$\underline{C}$C(CH$_3$)$_3$)

Compound 10

Compound 11

After 53.9 mg (0.108 mmol) of Compound 10 was mixed with 5 cm³ of dry pyridine, 38.4 mg (0.241 mmol) of sulfur trioxide-pyridine complex was added thereto. After stirring at 40° C. for 6 hours, 1 cm³ of methanol was added to the reaction mixture, and the mixture was passed through a column of Dowex 50W X8 (200 to 400 mesh) Na$^+$ type. The passed solution was concentrated under reduced pressure, and the residue was separated and purified by silica gel column chromatography (ethyl acetate-hexane) to thereby isolate Compound 11 (29.8 mg: 0.0499 mmol) as colorless crystals.
Compound 11:
Yield: 46%
Rf=0.625 (30% methanol-chloroform development once)
$^1$H NMR (400 MHz, CDCl$_3$) δ (ppm): 1.01 (s, 9H, C(C$\underline{H}_3$)$_3$), 1.16 (s, 9H, C(CH$_3$)$_3$), 1.93 (s, 3H, NHCOCH$_3$), 3.71 (s, 3H, OCH$_3$), 4.14 (d, J=9.9 Hz, 1H, H-6a), 4.31 (t, J=5.3 Hz, 1H, H-5), 4.49 (d, J=9.3 Hz, 1H, H-6b), 4.75 (td, J$_{2,3}$=J$_{2,NH}$=10.5 Hz, J$_{1,2}$=3.3 Hz, 1H, H-2), 5.02 (m, 1H, H-4), 5.27 (dd, J$_{2,3}$=10.5 Hz, J$_{3,4}$=1.8 Hz, 1H, H-3), 5.43 (d, J$_{1,2}$=3.3 Hz, 1H, H-1), 6.25 (br s, 1H, NH), 6.69 (d, J=8.7 Hz, 2H, arom. H) 6.87 (d, J=8.7 Hz, 2H, arom. H)
$^{13}$C NMR (100.4 MHz, CDCl$_3$) δ (ppm): 23.21 (q, NHCOC$\underline{H}_3$), 26.98 (q, C(C$\underline{H}_3$)$_3$), 27.06 (q, C(C$\underline{H}_3$)$_3$), 38.66 (s, $\underline{C}$(CH$_3$)$_3$), 39.01 (s, $\underline{C}$(CH$_3$)$_3$), 47.82 (d, C-2), 55.58 (q, O$\underline{C}$H$_3$), 64.46 (t, C-6), 69.12 (d, C-3), 69.12 (d, C-5), 73.20 (d, C-4), 97.27 (d, C-1), 114.56 (d, arom. CH), 118.42 (d, arom. CH), 150.31 (s, arom. C), 155.27 (s, arom. C), 170.51 (s, NHCOCH$_3$), 179.30 (s, O=$\underline{C}$C(CH$_3$)$_3$), 179.63 (s, O=$\underline{C}$C(CH$_3$)$_3$)

Compound 11

-continued

Compound 12

After 29.8 mg (0.0499 mmol) of Compound II was mixed with 1.0 cm³ of dry methanol, 0.10 cm³ of 1.0 mol dm⁻³ sodium methoxide methanol solution was added thereto. After stirring at room temperature for 48 hours, the reaction mixture was neutralized by using Amberlite IRC 50H⁺ type and concentrated under a reduced pressure. The residual material was purified by gel filtration (Superdex 30) to obtain 11.3 mg (0.0266 mmol) of Compound 12 (substance of the present invention).

Compound 12:

Yield: 53%

$^1$H NMR (400 MHz, D$_2$O) δ (ppm): 1.94 (s, 3H, NHCOCH$_3$), 3.63 (dd, J$_{6a,6b}$=11.8 Hz, J$_{5,6a}$=7.9 Hz, H-6a), 3.68 (dd, J$_{6a,6b}$=11.8 Hz, J$_{5,6b}$=4.4 Hz, H-6b), 3.69 (s, 3H, OCH$_3$), 4.12-4.16 (m, 2H, H-3 and H-5), 4.22 (dd, J$_{2,3}$=11.1 Hz, J$_{1,2}$=3.7 Hz, H-2), 4.69-4.72 (m, 1H, H-4), 5.41 (d, J$_{1,2}$=3.7 Hz, H-1), 6.84-6.88 (m, 2H, arom. H), 6.97-7.01 (m, 2H, arom. H)

$^{13}$C NMR (100.4 MHz, D$_2$O) δ (ppm): 24.76 (q, NHCOCH$_3$), 53.05 (d, C-2), 58.67 (q, OCH$_3$), 63.93 (t, C-6), 69.56 (d, C-3), 73.98 (d, C-5), 79.47 (d, C-4), 99.92 (d, C-1), 117.92 (d, arom. CH), 121.70 (d, arom. CH), 153.30 (s, arom. C), 157.56 (s, arom. C), 177.60 (s, NHCOCH$_3$)

Example 2

The enzyme activity was measured by modifying the method described in J. Biol. Chem., 276, 43894-43900 (2001). As the standard reaction solution, 2.5 µmol of imidazole-HCl (pH 6.8), 0.5 µmol of CaCl$_2$, 1 µmol of reduced type glutathione, 25 nmol in galactosamine equivalent of chondroitin sulfate A (derived from whale cartilage, manufactured by Seikagaku Corporation), 50 pmol of [$^{35}$S]PAPS (active sulfate: about 5.0×10$^5$ cpm: prepared according to Anal Biochem., 148, 303-310 (1985)), and human-derived GalNAc4S6ST prepared according to the method described in J. Biol. Chem., 276, 43894-43900 (2001) were added to 50 µl. The reaction was started by adding each of Substance 1 of the present invention, Substance 2 of the present invention, Substance 3 of the present invention, Substance 4 of the present invention, Substance 5 of the present invention and Substance 6 of the present invention to this reaction system to give a final concentration of 50 nmol, 125 nmol or 250 nmol.

The reaction was carried out by incubating the reaction solution at 37° C. for 20 minutes, and the reaction was terminated by heating the reaction tubes in boiling water for 1 minute. After termination of the reaction, 3 volumes of ethanol containing 1.3% potassium acetate was added thereto to thereby precipitate the $^{35}$S-labeled glycosaminoglycan, followed by gel chromatography using a high performance desalting column according to the method described in J. Biol. Chem., 268, 21968-21974 (1993), and then the radioactivity was measured by using a scintillation counter. A reaction system to which the enzyme was not added was used as the negative control.

Figure 1:
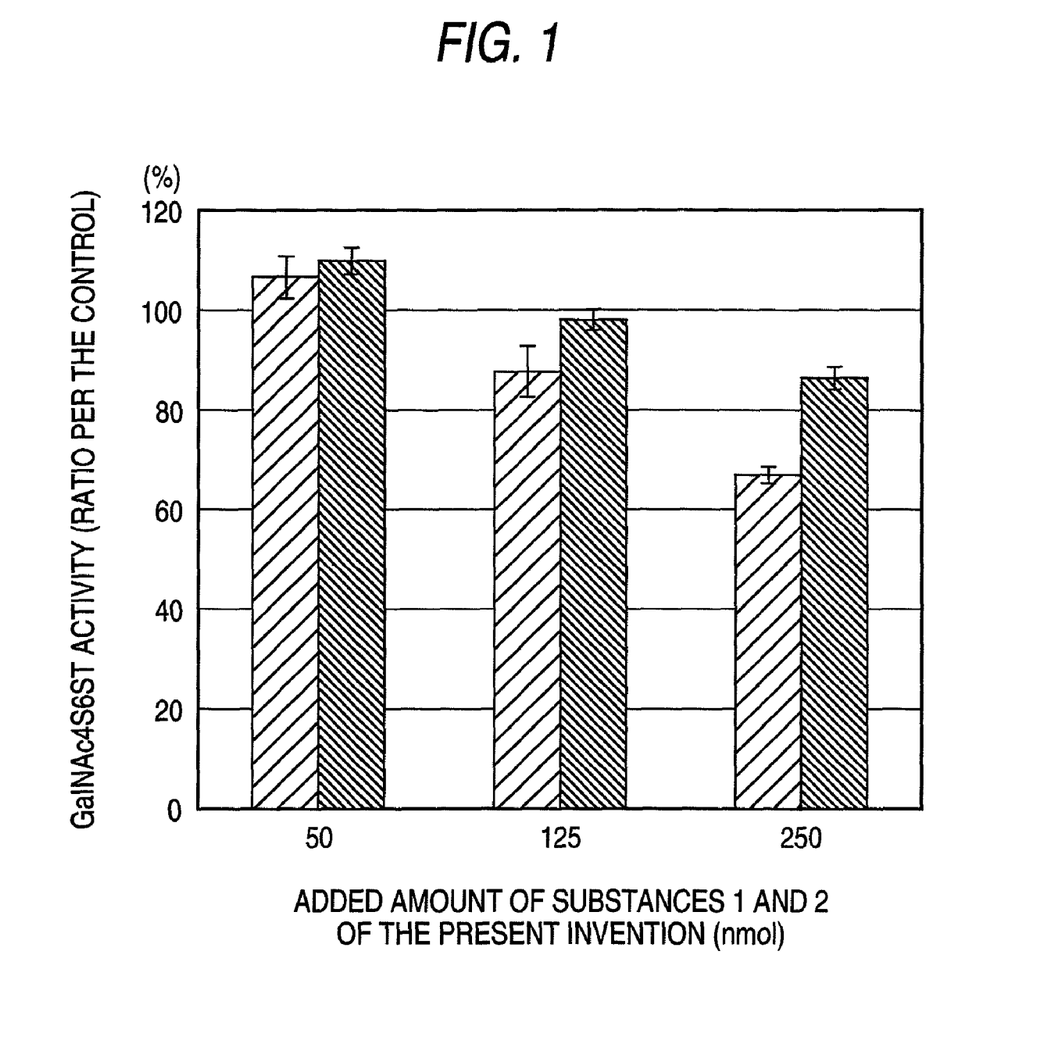
FIG. 1 is a graph showing inhibitory activity of Substance 1 of the present invention and Substance 2 of the present invention upon GalNAc4S6ST. Regarding the respective used amounts, the left side column indicates Substance 1 of the present invention, and the right side column indicates Substance 2 of the present invention.
Figure 2:
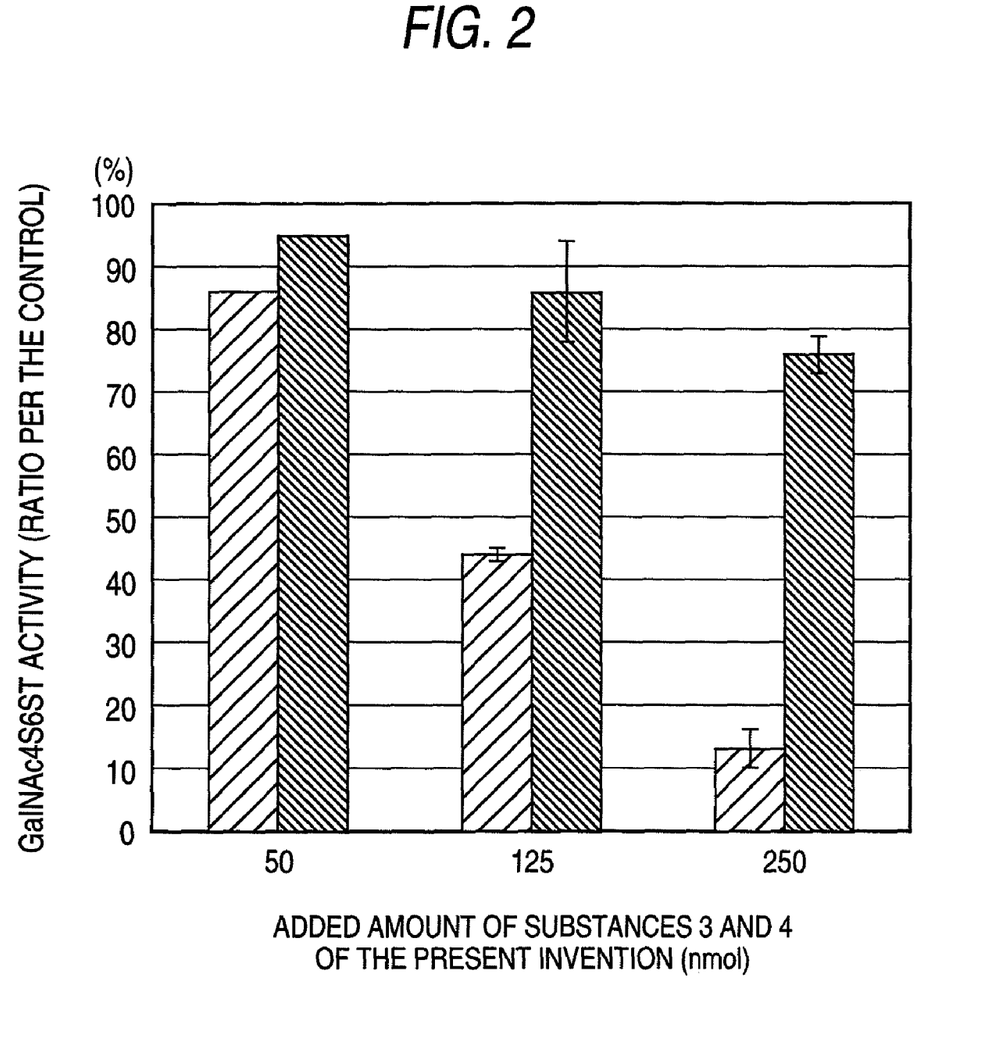
FIG. 2 is a graph showing inhibitory activity of Substance 3 of the present invention and Substance 4 of the present invention upon GalNAc4S6ST. Regarding the respective used amounts, the left side column indicates Substance 3 of the present invention, and the right side column indicates Substance 4 of the present invention.
Figure 3:
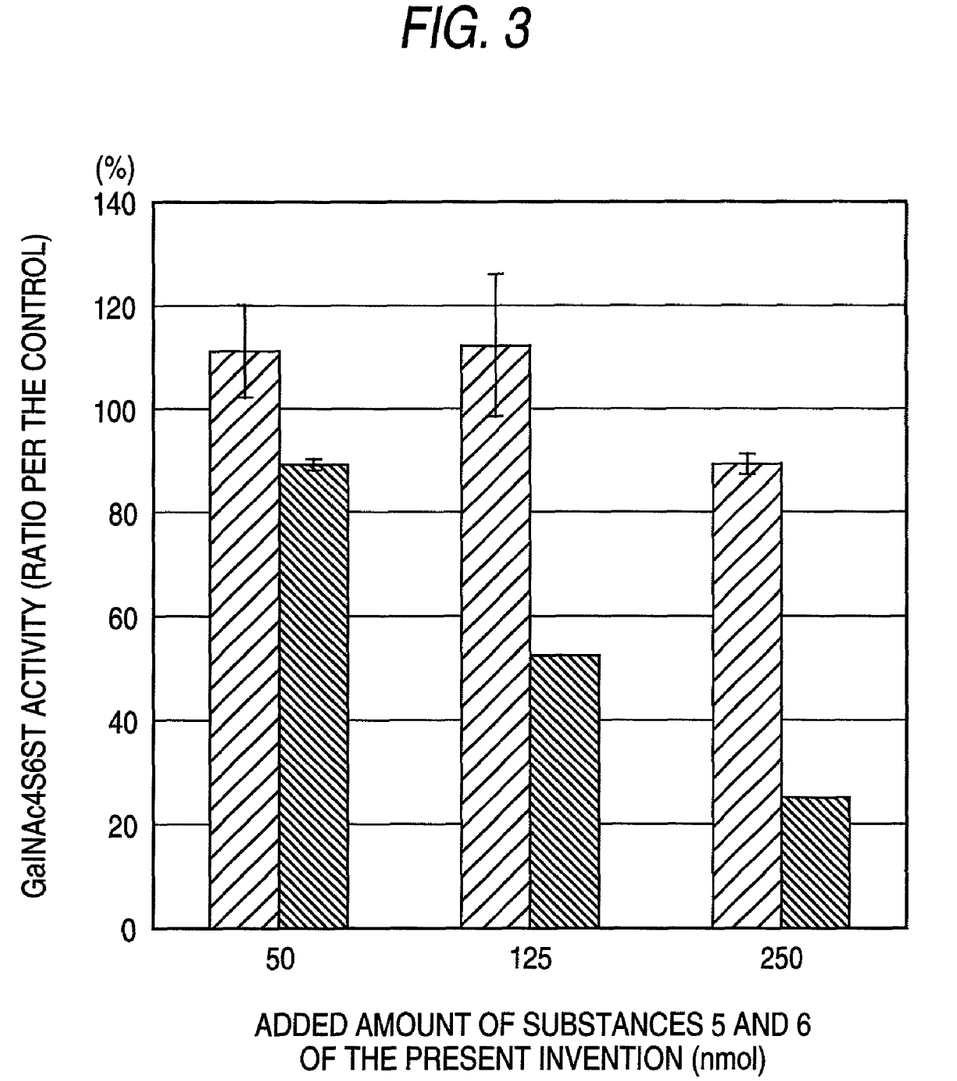
FIG. 3 is a graph showing inhibitory activity of Substance 5 of the present invention and Substance 6 of the present invention upon GalNAc4S6ST. Regarding the respective used amounts, the left side column indicates Substance 5 of the present invention, and the right side column indicates Substance 6 of the present invention.

By using the enzyme activity of a system to which the substance of the present invention was not added as the positive control and regarding it as 100%, relative values of the enzyme reaction in a system to which the substance of the present invention was added were calculated (Substance 1 of the present invention and Substance 2 of the present invention: FIG. 1, Substance 3 of the present invention and Substance 4 of the present invention: FIG. 2, Substance 5 of the present invention and Substance 6 of the present invention: FIG. 3).

As a result, the inhibitory activity was observed on both of Substance 1 of the present invention and Substance 2 of the present invention, and the inhibitory activity of Substance 2 of the present invention was particularly strong. In addition, the inhibitory activity was also observed regarding any one of the substances 3 to 6 of the present invention, and Substance 3 of the present invention showed stronger inhibitory activity when Substance 3 of the present invention (α type) and Substance 4 of the present invention (β type) were compared, while Substance 6 of the present invention showed stronger inhibitory activity when Substance 5 of the present invention (α type) and Substance 6 of the present invention (β type) were compared.

While the present invention has been described in detail and with reference to specific embodiments thereof, it will be apparent to one of skill in the art that various changes and modifications can be made therein without departing from the spirit and scope thereof.

This application is based on Japanese application Nos. 2002-201843 and filed on Jul. 10, 2002 and Dec. 27, 2002, respectively, the entire contents of which are incorporated hereinto by reference. All references cited herein are incorporated in their entirety.

INDUSTRIAL APPLICABILITY

The present invention provides a galactosamine derivative having activity of inhibiting a sulfotransferase and a sulfotransferase inhibitor using the same.

The invention claimed is:

1. A method for inhibiting activity of a sulfotransferase, which comprises contacting the galactosamine compound represented by the following formula (I):

wherein R$_1$, R$_2$ and R$_5$ each independently represents SO$_3^-$ or H, and at least one of them represents SO$_3^-$;
R$_3$ represents acetyl;
R$_4$ represents phenyl or methyoxyphenyl;
X represents O; and
∿∿ represents an α bond or a β bond,
with the sulfotransferase.

2. A method for inhibiting activity of a sulfotransferase, which comprises contacting the galactosamine compound represented by the following formula (I):

(1)

wherein $R_1$ and $R_5$ each represent H;
$R_2$ represents $SO_3$;
$R_3$ represents acetyl;
$R_4$ represents a phenyl, a naphthyl, an alkoxyphenyl, or a tolyl group;
X represents O; and
~~~ represents an α bond,
with the sulfotransferase.

3. A method for inhibiting activity of a sulfotransferase, which comprises contacting the galactosamine compound represented by the following formula (I):

(1)

wherein $R_2$ and $R_5$ each represent H;
$R_1$ represents $SO_3$;
$R_3$ represents acetyl;
$R_4$ represents a phenyl, a naphthyl, an alkoxyphenyl, or a tolyl group;
X represents O; and
~~~ represents a β bond,
with the sulfotransferase.

4. The method according to claim 1, wherein, $R_1$ and $R_5$ each represent H; and $R_2$ represents $SO_3^-$; and ~~~ represents an α bond.

5. The method according to claim 1, wherein $R_2$ and $R_5$ each represent H; and $R_1$ represents $SO_3^-$; and ~~~ represents a β bond.

6. A method for inhibiting a sulfation of a 6-position hydroxyl group of a chondroitin sulfate, wherein the sulfation occurs to the 6-position hydroxyl group of the 4-sulfated galactosamine residue in the chondroitin sulfate in the presence of a sulfotransferase,
the method comprising bringing the galactosamine compound represented by the following formula (I) to be in contact with the sulfotransferase coexistent with the chondroitin sulfate:

(1)

wherein $R_1$, $R_2$ and $R_5$ each independently represents $SO_3^-$ or H, and at least one of them represents $SO_3^-$;
$R_3$ represents acetyl;
$R_4$ represents phenyl or methoxyphenyl;
X represents O; and
~~~ represents an α bond or a β bond.

7. A method for inhibiting a sulfation of a 6-position hydroxyl group of a chondroitin sulfate, wherein the sulfation occurs to the 6-position hydroxyl group of the 4-sulfated galactosamine residue in the chondroitin sulfate in the presence of a sulfotransferase,
the method comprising bringing the galactosamine compound represented by the following formula (I) to be in contact with the sulfotransferase coexistent with the chondroitin sulfate:

(1)

wherein, $R_1$ and $R_5$ each represent H;
$R_2$ represents $SO_3$;
$R_3$ represents acetyl;
$R_4$ represents an aryl which is optionally substituted by an alkyl group or $R_4$ represents a phenyl, a naphthyl, an alkoxyphenyl, or a tolyl group;
X represents O; and
~~~ represents an α bond.

8. A method for inhibiting a sulfation of a 6-position hydroxyl group of a chondroitin sulfate, wherein the sulfation occurs to the 6-position hydroxyl group of the 4-sulfated galactosamine residue in the chondroitin sulfate in the presence of a sulfotransferase,
the method comprising bringing the galactosamine compound represented by the following formula (I) to be in contact with the sulfotransferase coexistent with the chondroitin sulfate:

(1)

wherein $R_2$ and $R_5$ each represent H;
$R_1$ represents $SO_3$;
$R_3$ represents acetyl;
$R_4$ represents an aryl which is optionally substituted by an alkyl group or $R_4$ represents a phenyl, a naphthyl, an alkoxyphenyl, or a tolyl group;

X represents O; and

∿ represents a β bond.

9. The method according to claim 6, wherein, $R_1$ and $R_5$ each represent H; and $R_2$ represents $SO_3^-$; and ∿ represents an α bond.

10. The method according to claim 6, wherein $R_2$ and $R_5$ each represent H; and $R_1$ represents $SO_3^-$; and ∿ represents a β bond.

* * * * *